(12) United States Patent
Ashida et al.

(10) Patent No.: US 6,551,249 B2
(45) Date of Patent: Apr. 22, 2003

(54) SPHYGMOMANOMETER CUFF

(75) Inventors: Tameo Ashida, Kyoto (JP); Norihito Yamamoto, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 10/009,193

(22) PCT Filed: May 10, 2001

(86) PCT No.: PCT/JP01/03915
§ 371 (c)(1),
(2), (4) Date: Dec. 10, 2001

(87) PCT Pub. No.: WO01/85026
PCT Pub. Date: Nov. 15, 2001

(65) Prior Publication Data
US 2002/0161303 A1 Oct. 31, 2002

(30) Foreign Application Priority Data
May 12, 2000 (JP) ....................... 2000-139334

(51) Int. Cl.⁷ ................................................ A61B 5/00
(52) U.S. Cl. ...................... 600/499; 606/202
(58) Field of Search ............................ 600/499; 606/202

(56) References Cited
U.S. PATENT DOCUMENTS 3,654,931 A    4/1972  Hazlewood
3,669,096 A *  6/1972  Hurwitz ........................ 600/499
3,906,937 A *  9/1975  Aronson ....................... 600/499
4,745,924 A *  5/1988  Ruff ............................. 600/499
5,797,851 A    8/1998  Byrd
6,245,023 B1 * 6/2001  Clemmons .................. 600/499

FOREIGN PATENT DOCUMENTS

| EP | 0 274 735 | 7/1988 |
| JP | 2-116406 | 9/1990 |
| JP | 3-45687 | 9/1991 |

* cited by examiner

Primary Examiner—Robert L. Nasser
(74) Attorney, Agent, or Firm—Morrison & Foerster LLP

(57) ABSTRACT

A sphygmomanometer cuff (10A) having an air bag (12) arranged within an outer bag (11), from which a tube (13) attached to the air bag (12) is extended outward, is provided. The outer bag (11) is provided with an opening portion (15) for replacing the air bag, and an anti-rotating member (20) for preventing rotation of the air bag (12) within the outer bag (11) is provided at a tube attaching portion (17) of the air bag (12) or at the vicinity thereof. The tube (13) of the air bag (12) is drawn out of the outer bag (11) through the opening portion (15). This structure allows replacement of the air bag (12) and, in addition, prevents any inconvenience such as winding of the air bag (12) within the outer bag and the like.

7 Claims, 9 Drawing Sheets

SPHYGMOMANOMETER CUFF

This is a continuation of PCT/JP01/03915, filed May 10, 2001.

TECHNICAL FIELD

The present invention relates to a sphygmomanometer cuff that is wrapped around a human upper arm in measuring blood pressure to apply pressure necessary for measuring blood pressure.

BACKGROUND ART

A sphygmomanometer cuff generally consists of an outer bag 70 having a pair of strip-like cloth material overlapped and joined at the outer periphery, and an air bag 72 arranged within this outer bag 70, as shown in FIG. 10. A tube 73 is attached to air bag 72 for inflating/deflating the air bag. Tube 73 is drawn out of outer bag 70 and connected to a sphygmomanometer body.

Recently, in order to improve the sensitivity to detect pulse waves, air bag 72 is formed of vinyl chloride. Because of its feature of being thin, however, air bag 72 made of vinyl chloride may wind around tube 73 when used over years as shown in FIG. 10.

In order to solve this problem, Japanese Utility-Model Laying-Open No. 2-116406 discloses a sphygmomanometer cuff, in which an outer bag 80 and a thin-walled air bag 81 arranged in outer bag 80 are integrally adhered as shown in FIG. 11. This adhered portion is, for example, at a tube attaching portion of air bag 81 (i.e. a coupling part of air bag 81 to tube 83) or at opposing ends 86 of air bag 81. Outer bag 80 and air bag 81 are made integral at these parts 85 or 86, for example, by hot welding. The above noted publication also discloses that the tube attaching portion of air bag 81 is provided with a projecting piece, which is adhered to outer bag 80.

In the cuff described in the above noted publication, however, outer bag 80 and air bag 81 are partially adhered and fixed each other. Therefore, when air bag 81 is fractured, air bag 81 cannot be replaced. Further, when outer bag, which is susceptible to contamination, is to be washed, air bag 81 cannot be removed from outer bag 80. In other words, once air bag 81 is fractured, even outer bag 80 must also be replaced, resulting in waste of resources. In addition, to wash outer bag 80 is difficult.

DISCLOSURE OF THE INVENTION

In order to solve the above noted conventional problems, an object of the present invention is to provide a sphygmomanometer cuff allowing replacement of an air bag and also preventing such an inconvenience as winding of the air bag within an outer bag and the like.

A sphygmomanometer cuff to achieve the above noted object has an air bag arranged within an outer bag, from which a tube attached to the air bag is extended outward. The outer bag is provided with an opening portion for replacing the air bag. An anti-rotating member for preventing rotation of the air bag within the outer bag is provided on at least one of a tube attaching portion of the air bag and the vicinity thereof. The tube of the air bag is drawn out of the outer bag through the opening portion.

Since the outer bag has the opening for replacing the air bag in this cuff, the air bag can be easily taken in and out through the opening portion, and replacement of the air bag is realized. Further, since the air bag has the anti-rotating member at the tube attaching portion or at the vicinity thereof, the air bag will not be displaced within the outer bag, thus eliminating any inconvenience such as winding of the air bag etc., even if torsion force is exerted on the tube with the air bag arranged within the outer bag, or the cuff is repeatedly stored away with the tube twisted.

It is noted that, though the opening portion of the outer bag for replacing the air bag may not provide opening/closing, a fastener for opening and closing the opening portion may be provided at the opening portion excluding an exit of the tube, to close the opening portion when the air bag is placed in the outer bag. Furthermore, since the fastener is not provided at the tube exit, the tube exit can be easily found when the air bag is put into the outer bag, and thus the air bag will not be placed inside out.

The anti-rotating member provided at the tube attaching portion of the air bag or at the vicinity thereof is not limited in its shape and material, as long as it has an effect of preventing rotation of the air bag within the outer bag. Conveniently, the anti-rotating member includes a fastener when the opening portion is provided with a fastener. Specifically, in such a case, when the fastener of the anti-rotating member and the fastener of the opening portion are made engageable with each other, it would be convenient for use.

In the sphygmomanometer cuff of the present invention, the anti-rotating member is fixed to the tube attaching portion of the air bag, for example, by hot welding.

Furthermore, in a preferred embodiment of the present invention, the anti-rotating member is expanded from the tube attaching portion to the surface of the air bag. In this case, the anti-rotating member can be fixed to the tube attaching portion by hot welding, and to the surface of the air bag by adhesion.

BEST MODES FOR CARRYING OUT THE INVENTION

In the following, embodiments of the present invention will be described with reference to the drawings.

First, a sphygmomanometer cuff 10A in accordance an embodiment of the present invention will be described with reference to FIGS. 1 to 6.

Figure 1:
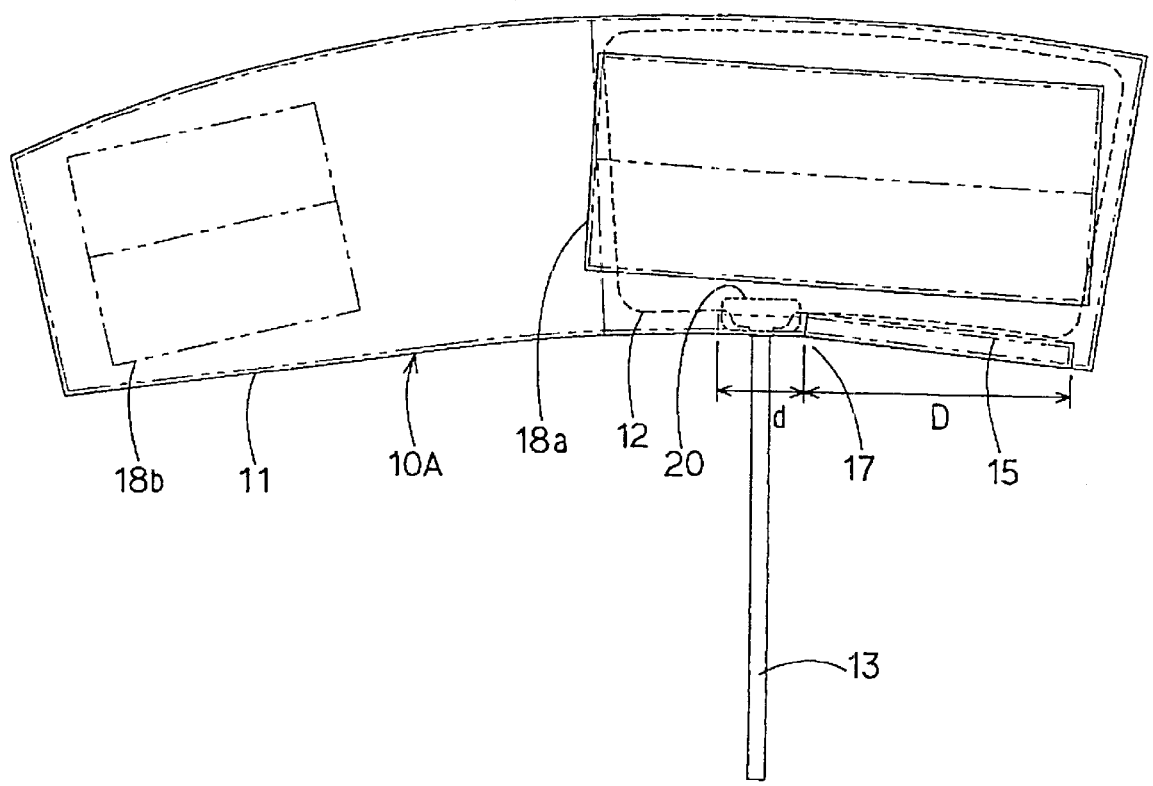
FIG. 1 is a plan view of the inside of a sphygmomanometer cuff in accordance with an embodiment of the present invention.
Figure 2:
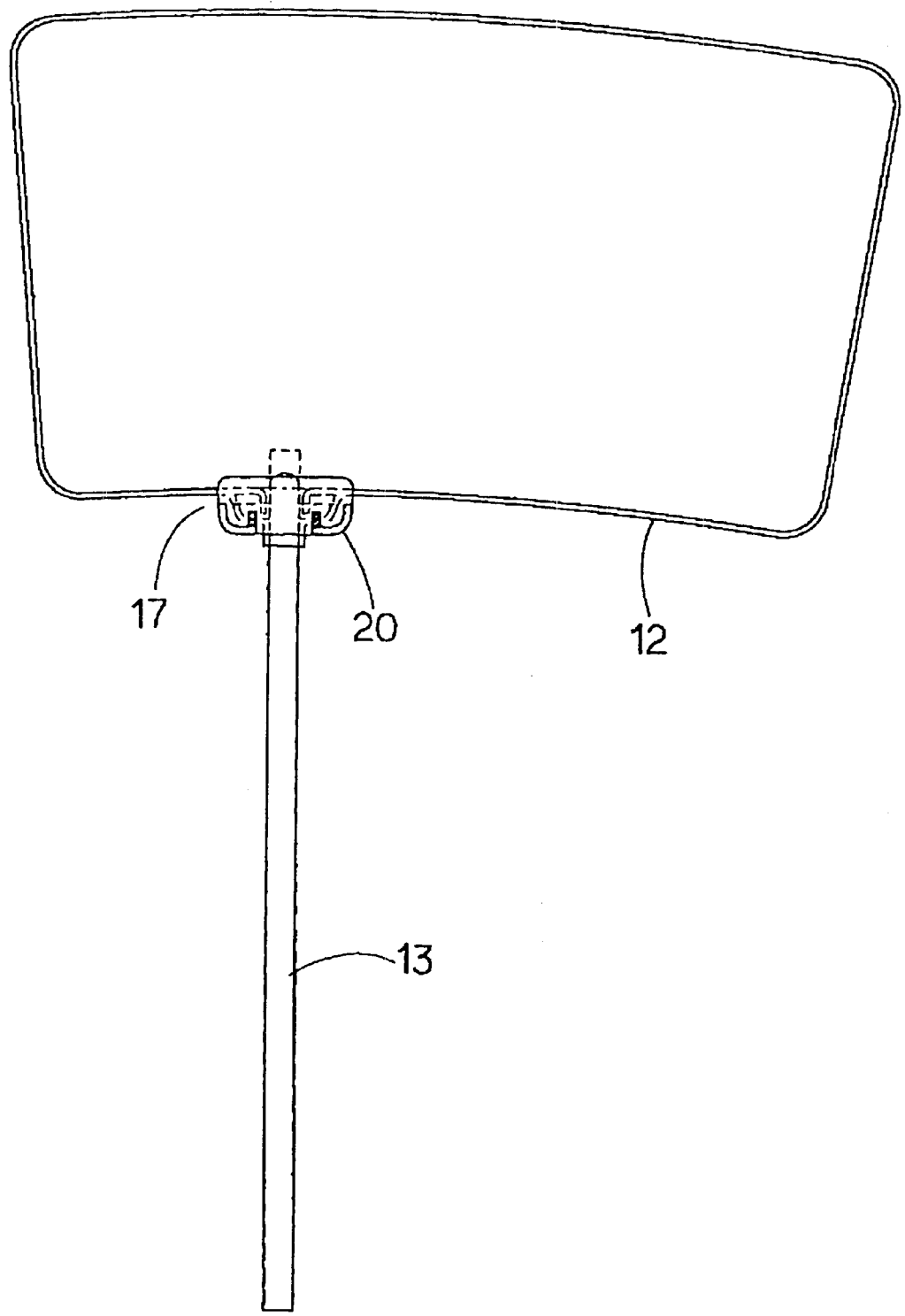
FIG. 2 is a plan view of an air bag of the cuff shown in FIG. 1.
Figure 3:
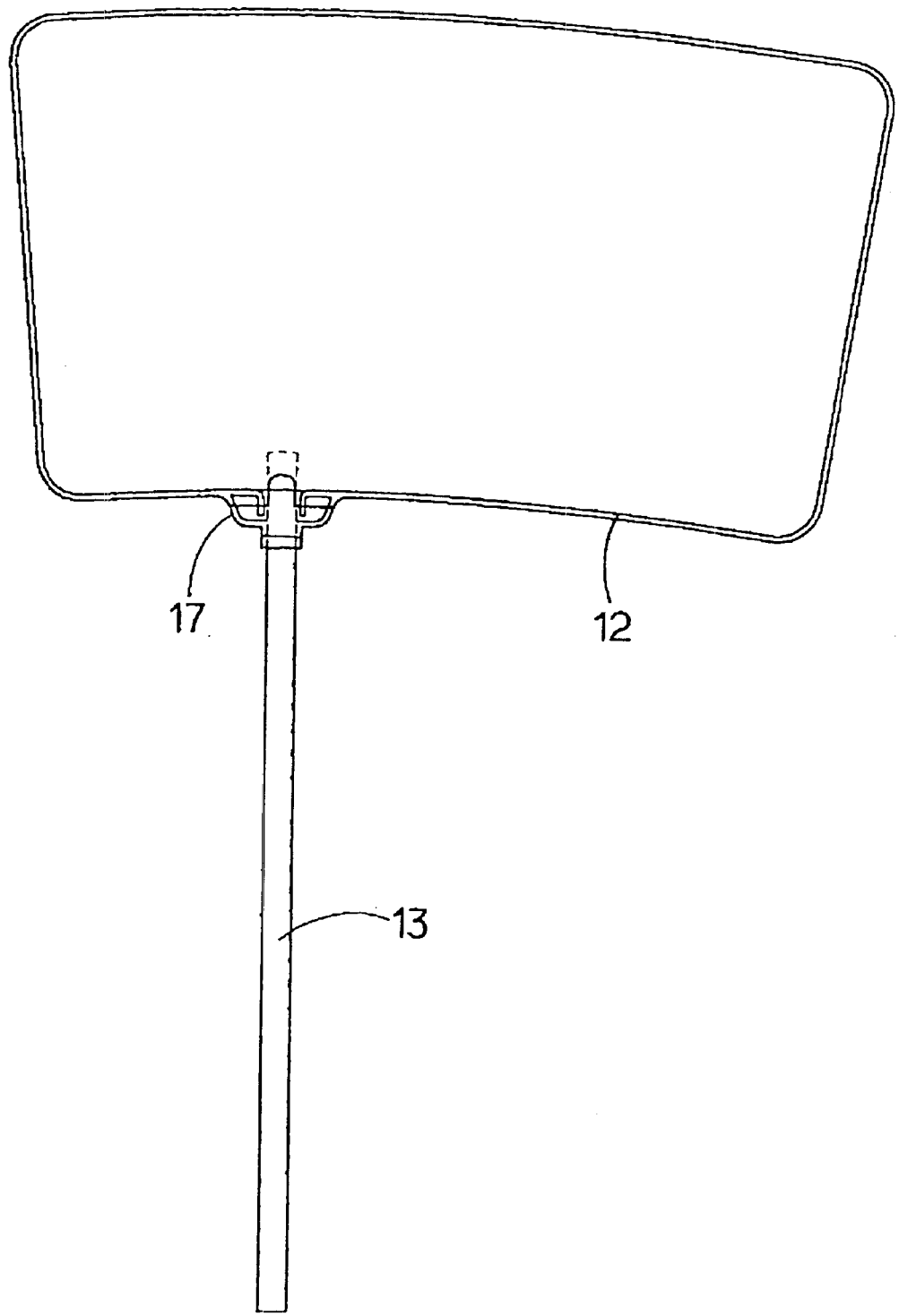
FIG. 3 is a plan view of the air bag shown in FIG. 2 with an anti-rotating member removed from a tube attaching portion.

As shown in FIG. 1, sphygmomanometer cuff 10A of the present embodiment includes an outer bag 11, an air bag 12 arranged within outer bag 11, and a tube 13 attached to air bag 12 and drawn out of outer bag 11 to extend outward. In this sphygmomanometer cuff 10A, the outer bag is provided with an opening portion for replacing the air bag, and an anti-rotating member 20 is provided at a tube attaching portion 17 of air bag 12 for preventing rotation of air bag 12 within outer bag 11. Further, through opening portion 15 of outer bag 11, tube 13 of air bag 12 is drawn out of outer bag 11 to extend outward.

Outer bag 11 is formed, for example, by joining the outer periphery of a pair of strip-like cloth material as mentioned above. Air bag 12 is arranged in the inner space provided on one side in the longitudinal direction (on the right side in FIG. 1) of the outer bag. The inside and outside of outer bag 11 are respectively provided with hook-and-loop fasteners 18a, 18b, which secure cuff 10A wrapped around a certain region of living body.

The right side in the longitudinal direction of outer bag 11 is provided with opening portion 15 for replacing the air bag, having a length of width d plus width D. Since the part of width d of this opening portion provides a tube exit (including anti-rotating member 20 here), this part is not provided with a fastener (not shown), whereas the part of width D is provided with a fastener. An example of fasteners includes one having protrusions on one side and recesses on the other side fitted in together, and one having teeth arranged oppositely to be mated together by means of a slider. Further, in stead of using a fastener, the opening portion may be closed up by means of a button.

Figure 4A:
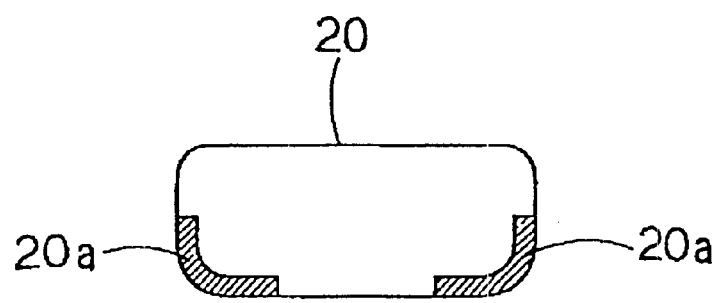
FIG. 4A is a plan view of the anti-rotating member provided at the tube attaching portion of the air bag shown in FIG. 2.
Figure 4B:
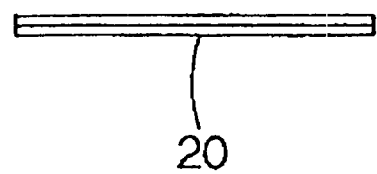
FIG. 4B is a side view of FIG. 4A.

Air bag 12 is formed, for example, with a thin film of vinyl chloride and has tube attaching portion 17 where tube 13 is attached. Tube 13 is drawn out of outer bag 11 to extend outward and connect to a sphygmomanometer body. Anti-rotating member 20 provided at tube attaching portion 17 has such a shape as shown in FIG. 4. This anti-rotating member is fixed to tube attaching portion 17 of air bag 12, for example, by high-frequency welding at hatched part 20a shown in the drawing.

As shown in FIG. 1, tube attaching portion 17 is disposed at the part of width d of opening portion 15 of outer bag 11. Air bag 12 is accommodated in outer bag 11 with anti-rotating member 20 located at tube attaching portion 17, and the part of width D of opening portion 15 is closed by a fastener. In this state, even if torsion force is exerted on tube 13, anti-rotating member 20 abuts against opening portion 15, so that the torsion force from tube 13 does not act on air bag 12 to displace air bag 12 within outer bag 11. As a result, any inconvenience such as winding of air bag 12 and the like does not occur.

Furthermore, width d, that is, that part of opening portion 15 of outer bag 11 which is not provided with a fastener, provides an exit for tube 13, where anti-rotating member 20 is positioned. Therefore, when air bag 12 is put into outer bag 11, the exit of tube 13 can be easily found, and thus air bag 12 will not put into outer bag 11 inside out. In addition, it is possible to keep opening portion 15 closed by means of a fastener except when air bag 12 is taken out of outer bag 11.

Figure 5:
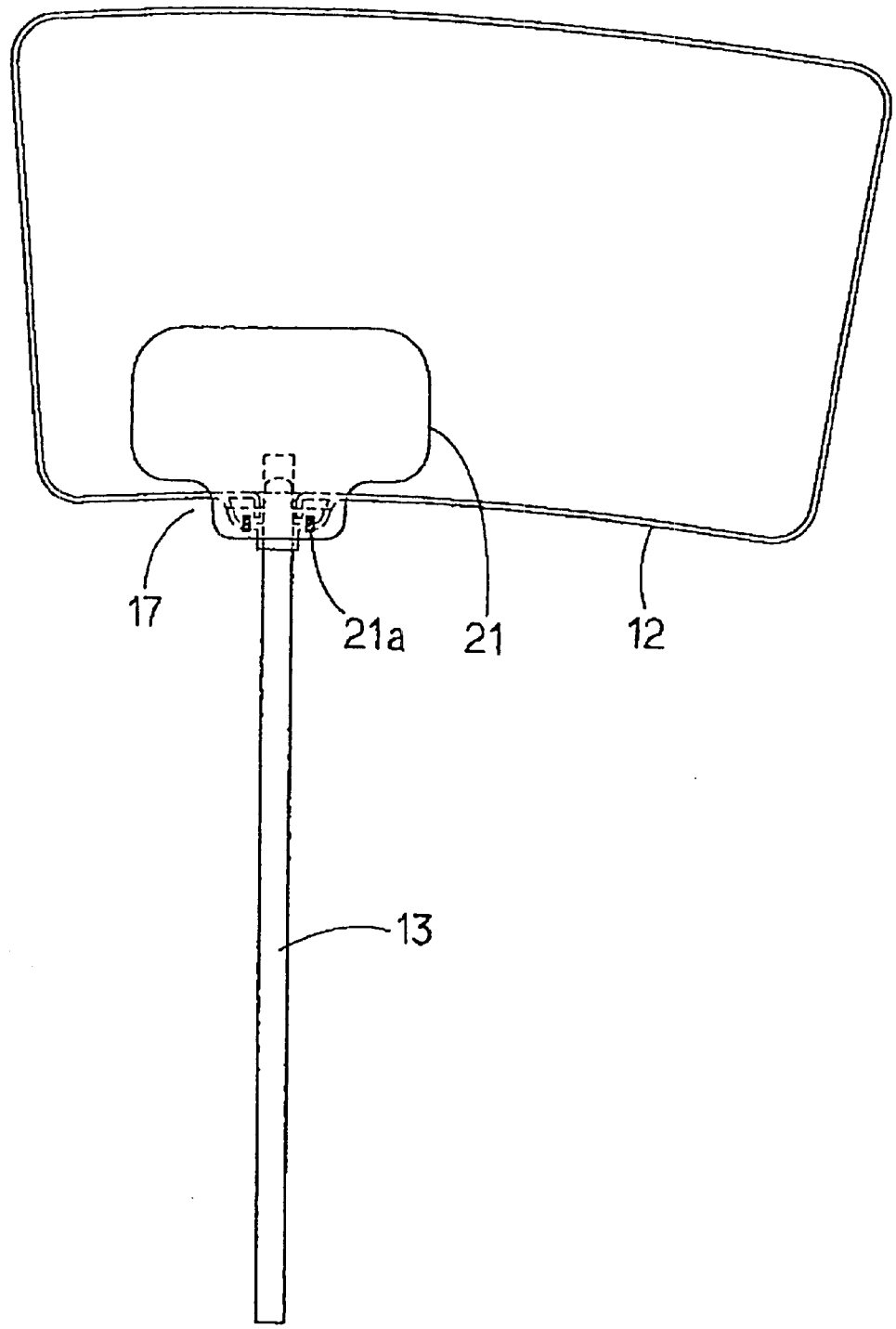
FIG. 5 is a plan view of the air bag having a modified anti-rotating member provided at the tube attaching portion.
Figure 6:
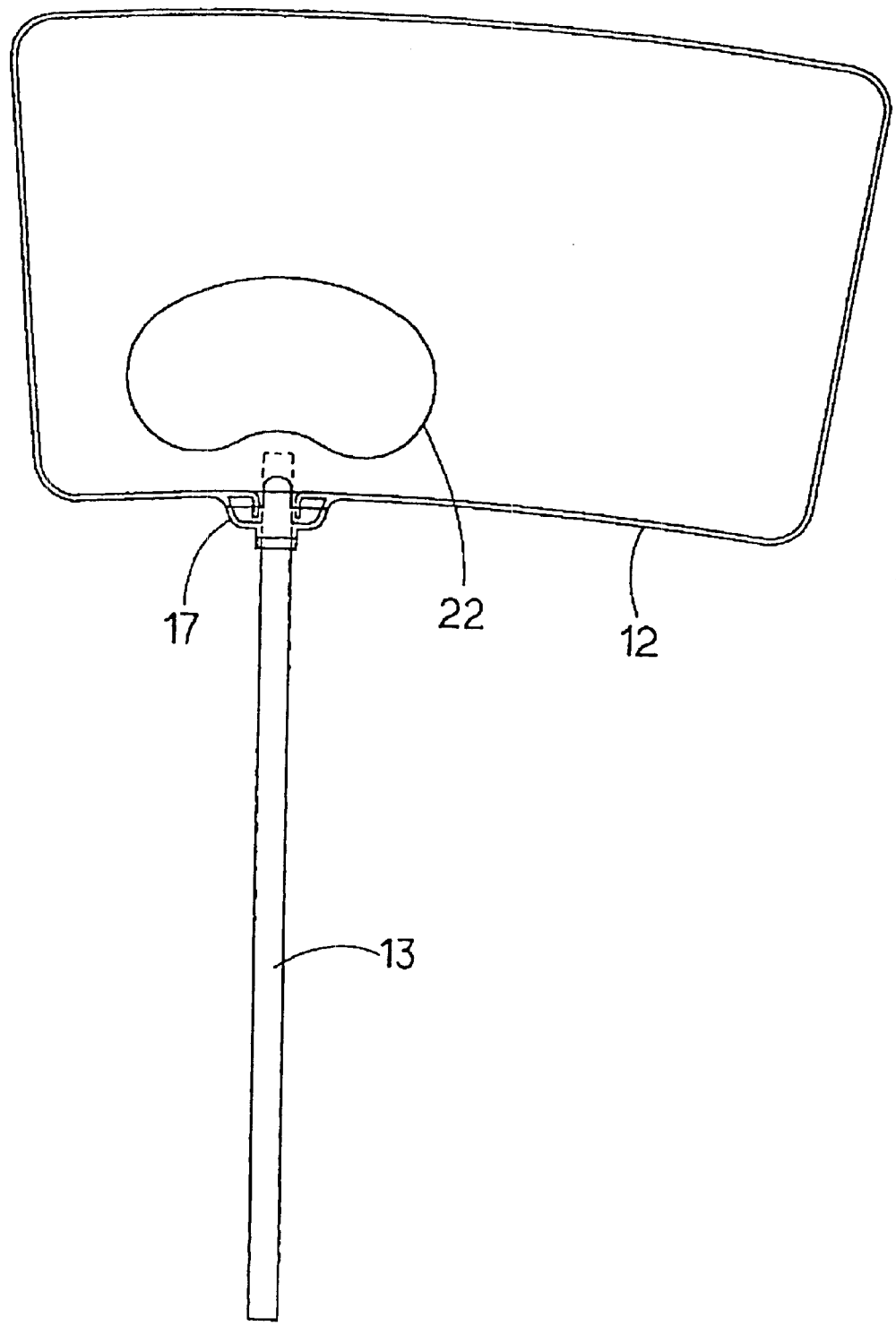
FIG. 6 is a plan view of the air bag having another modified anti-rotating member provided in the vicinity of the tube attaching portion.

FIGS. 5 and 6 show two modifications of the anti-rotating member. In case of cuff 10A of the above noted embodiment, anti-rotating member 20 is provided only at tube attaching portion 17 of air bag 12. On the other hand, in accordance with a modified embodiment shown in FIG. 5, anti-rotating member 21 of air bag 12 is not only provided at tube attaching portion 17 but also expanded to the surface of air bag 12, wherein anti-rotating member 21 is hot-welded using high-frequency at hatched part 21a, and adhered to the surface of air bag 12. Since this anti-rotating member 21 extends to the outer side of air bag 12, any inconvenience such as winding of air bag 12 can be prevented even more effectively.

In accordance with another modification shown in FIG. 6, anti-rotating member 22 of air bag 12 is not provided at tube attaching portion 17 but adhered to one face of air bag 12 in the vicinity of tube attaching portion 17. In this case, anti-rotating member 22 is formed of vinyl chloride sheet, rubber sheet or the like, having such a thickness that cannot be easily deformed. When air bag 12 with this anti-rotating member 22 thereon is placed inside outer bag 11, anti-rotating member 22 performs a function of preventing deformation, and therefore any inconvenience such as winding of air bag 12 and the like does not occur as well.

Figure 9:
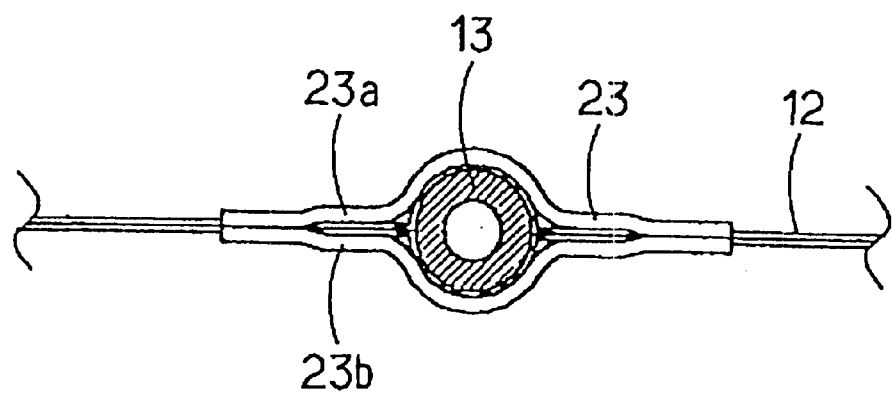
FIG. 9 is a partial side view of FIG. 8 seen from a direction of arrow A.
Figure 7:
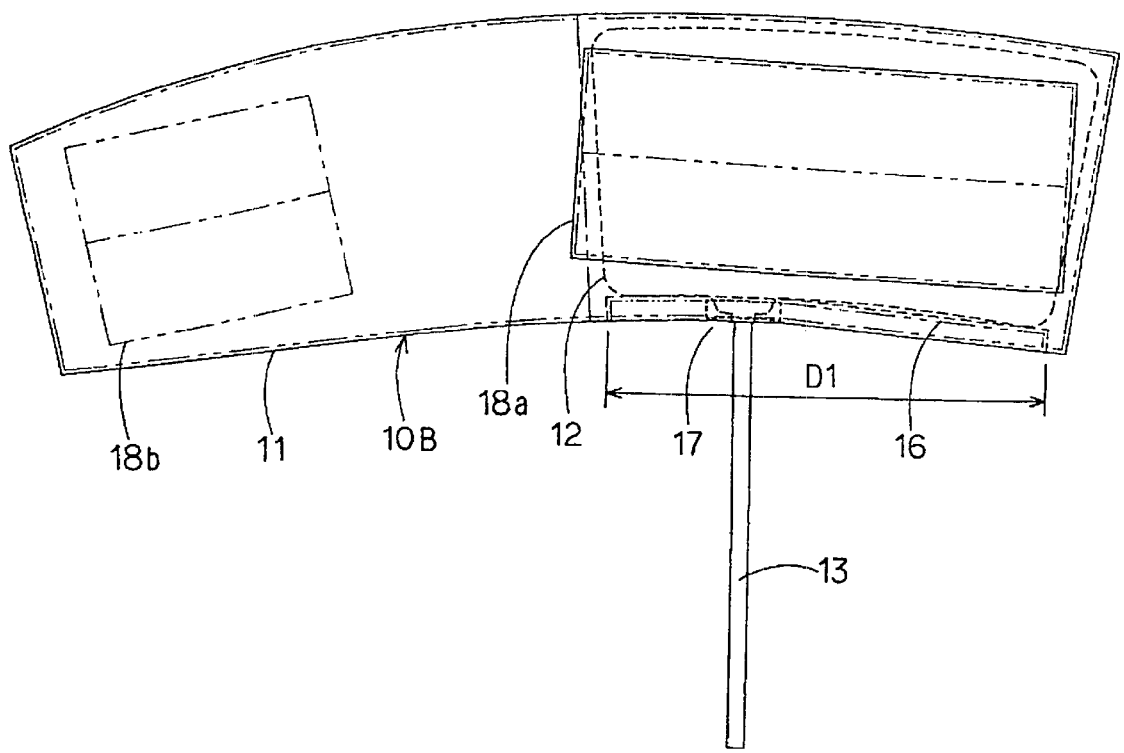
FIG. 7 is a plan view of the interior of a sphygmomanometer cuff in accordance with another embodiment of the present invention.
Figure 8:
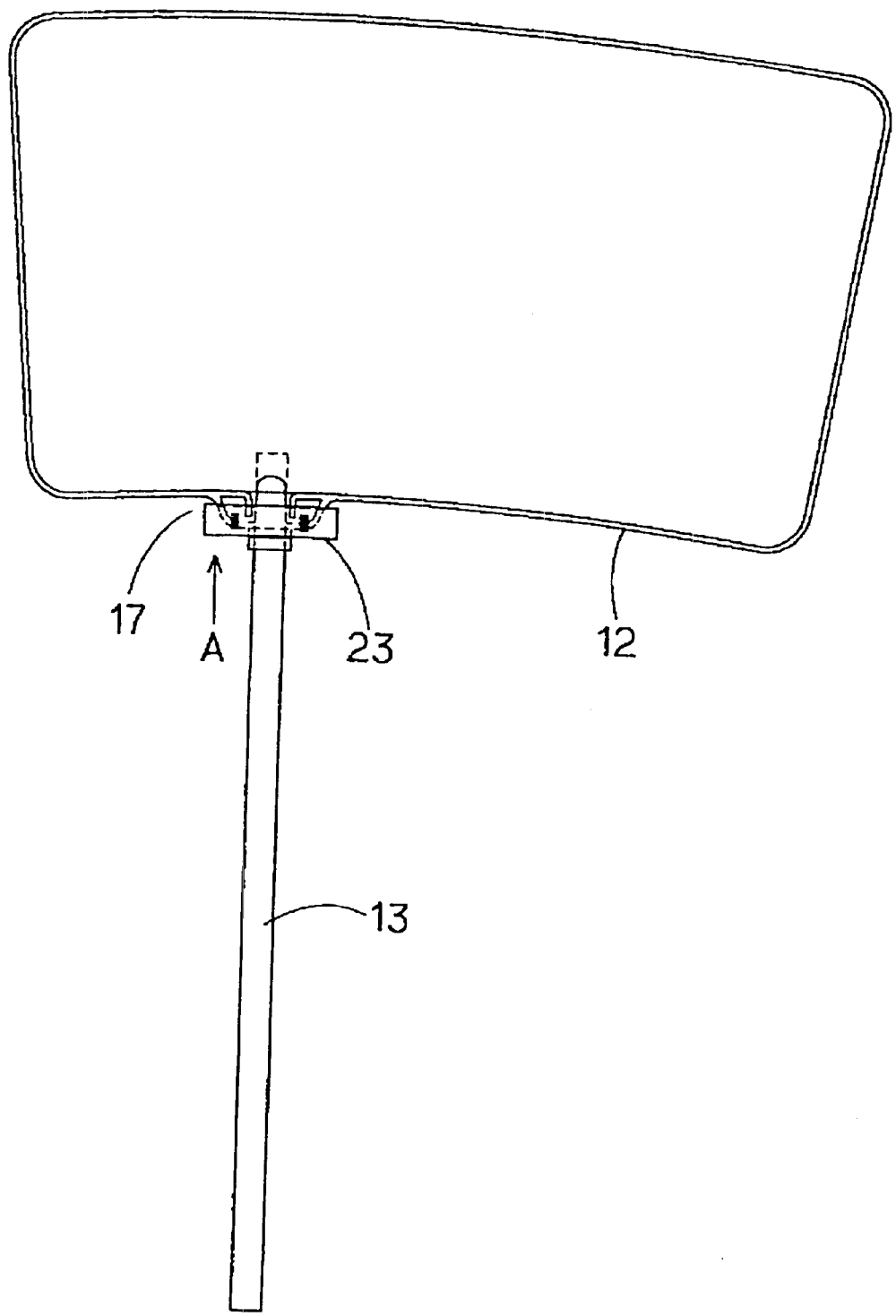
FIG. 8 is a plan view of an air bag of the cuff shown in FIG. 7.
Figure 10:
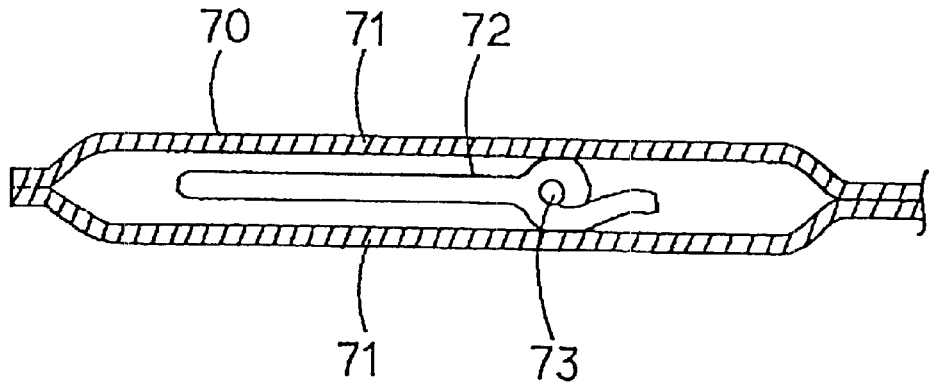
FIG. 10 is a partial cross-sectional view of a conventional sphygmomanometer cuff.
Figure 11:
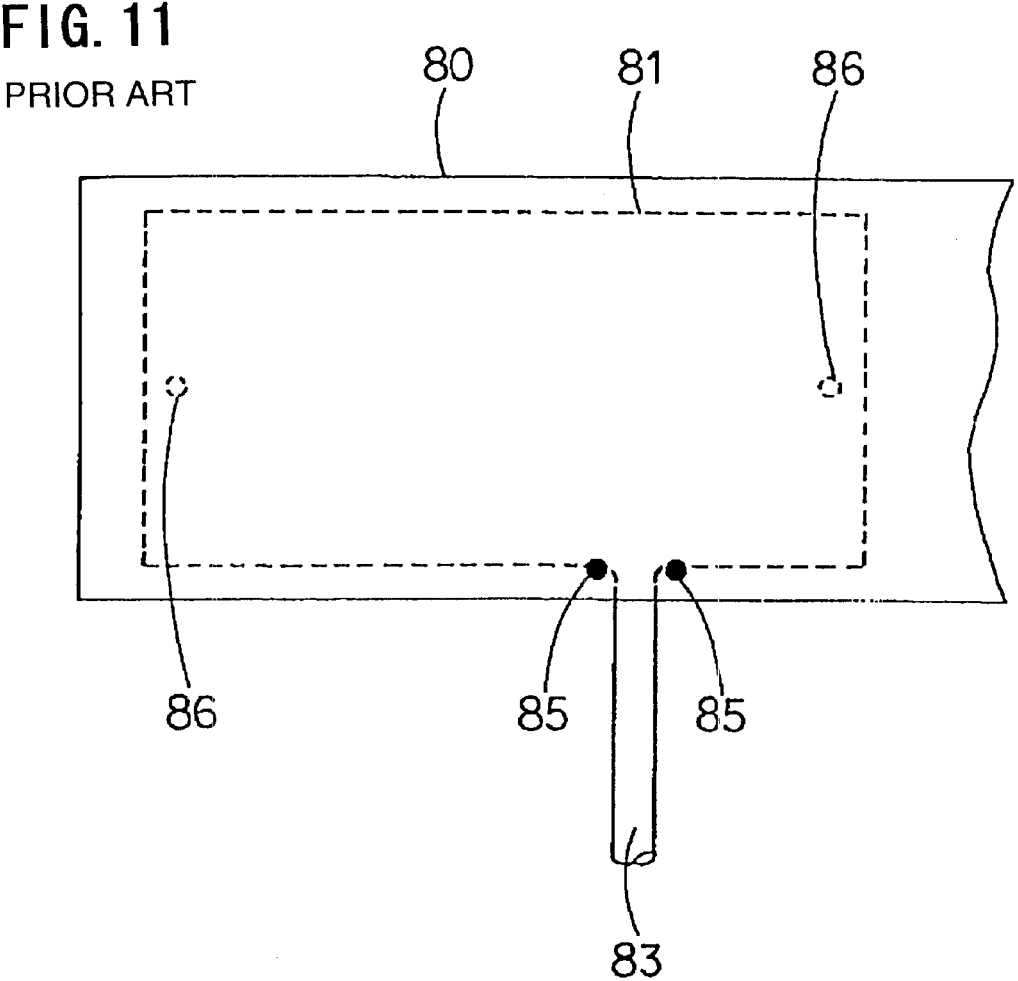
FIG. 11 is a partial plan view of another conventional sphygmomanometer cuff.

Sphygmomanometer cuff 10B in accordance with another embodiment of the present invention will now be described with reference to FIGS. 7 to 9. FIG. 7 shows a plan view of the inside of sphygmomanometer cuff 10B, FIG. 8 shows a plan view of the air bag thereof, and FIG. 9 shows a partial side view of FIG. 8 seen from a direction of arrow A. Note that the same element with the above noted cuff 10A is denoted with the same reference character. In the sphygmomanometer cuff 10B in accordance with the present embodiment, opening portion 16 of outer bag 11 for replacing the air bag is provided across almost the entire width D1 of the space where air bag 12 is accommodated. Anti-rotating member 23 provided at tube attaching portion 17 of air bag 12 has a fastener function.

As shown in FIG. 9, anti-rotating member 23 forms a fastener having a protruding portion at one piece 23a and a recess portion at other piece 23b. The protruding portion and the recess portion can be fitted in together for closing. This anti-rotating member 23 can be engaged with the same type of fastener provided at opening portion 16 of outer bag 11. When air bag 12 is accommodated in outer bag 11 with anti-rotating member 23 located at opening portion 16, and the fastener of opening portion 16 as well as the fastener of anti-rotating member 23 are dosed consecutively, tube 13 is extended outward through opening portion 16 as shown in FIG. 7. With the structure of this embodiment, any inconvenience such as winding of air bag 12 and the like can also be prevented by the effect of anti-rotating member 23, similar to the above noted cuff 10A.

Note that, cuffs 10A and 10B of the above noted embodiments show that anti-rotating members 20–23 are provided only at either tube attaching portion 17 or the vicinity thereof. Alternatively, they may be provided at both of them to improve a function of preventing rotation of air bag 12.

Although the present invention has been described and illustrated in detail, it is clearly understood that the same is by way of illustration and example only and is not to be taken by way of limitation, the spirit and scope of the present invention being limited only by the terms of the appended claims.

INDUSTRIAL APPLICABILITY

As described above, a sphygmomanometer cuff in accordance with the present invention provides that an outer bag has an opening portion for replacing an air bag, so that the air bag can easily be taken in and out through the opening portion to facilitate replacement of the air bag. Further, since the air bag has an anti-rotating member at a tube attaching portion or at the vicinity thereof, the air bag will not be displaced within the outer bag, and any inconvenience such as winding of the air bag and the like will not occur.

What is claimed is:

1. A sphygmomanometer cuff, comprising:
   an outer bag having an opening portion provided therein for allowing replacement of the air bag,
   an air bag arranged within the outer bag and including a tube attaching portion,
   a tube attached to the air bag and extending outward, and
   an anti-rotation member for preventing rotation of the air bag within the outer bag provided on the tube attaching portion of the air bag or in the vicinity thereof, the tube of the air bag being drawn out of the outer bag through the opening portion.

2. The sphygmomanometer cuff according to claim 1, further comprising a fastener for opening and closing the opening portion provided at the opening portion of the outer bag.

3. The sphygmomanometer cuff according to claim 1, wherein the anti-rotating member includes a fastener.

4. The sphygmomanometer cuff according to claim 2, wherein the anti-rotating member includes a fastener which can engage with the fastener provided at the opening portion of the outer bag.

5. The sphygmomanometer cuff according to claim 1, wherein the anti-rotating member is fixed to the tube attaching portion of the air bag by hot welding.

6. The sphygmomanometer cuff according to claim 1, wherein the anti-rotating member is expanded from the tube attaching portion to the surface of the air bag.

7. The sphygmomanometer cuff according to claim 6, wherein the anti-rotating member is fixed to the tube attaching portion of the air bag by hot welding and adhered to the surface of the air bag.

* * * * *